United States Patent [19]

Crocco et al.

[11] Patent Number: 5,693,834
[45] Date of Patent: Dec. 2, 1997

[54] INTEGRATED PROCESS FOR EPOXIDATION

[75] Inventors: Guy L. Crocco, Wilmington, Del.; John C. Jubin, Jr., West Chester; John G. Zajacek, Devon, both of Pa.

[73] Assignee: ARCO Chemical Technology, L.P., Greenville, Del.

[21] Appl. No.: 404,657

[22] Filed: Mar. 15, 1995

[51] Int. Cl.⁶ .................................................. C07D 301/12
[52] U.S. Cl. ................................................................ 549/531
[58] Field of Search ................................................ 549/531

[56] References Cited

U.S. PATENT DOCUMENTS

| | | | |
|---|---|---|---|
| 3,953,362 | 4/1976 | Lines et al. | 252/431 N |
| 4,009,122 | 2/1977 | Lines et al. | 252/431 N |
| 4,157,346 | 6/1979 | Lines et al. | 260/348.31 |
| 4,824,976 | 4/1989 | Clerici et al. | 549/531 |
| 4,833,260 | 5/1989 | Neri et al. | 549/531 |
| 5,214,168 | 5/1993 | Zajacek et al. | 549/531 |
| 5,221,795 | 6/1993 | Clerici et al. | 549/531 |
| 5,252,758 | 10/1993 | Clerici et al. | 549/531 |
| 5,262,550 | 11/1993 | Crocco et al. | 549/531 |
| 5,354,875 | 10/1994 | Nemeth et al. | 549/531 |
| 5,374,747 | 12/1994 | Saxton et al. | 549/531 |
| 5,384,418 | 1/1995 | Zajacek et al. | 549/531 |
| 5,412,122 | 5/1995 | Saxton et al. | 549/531 |

*Primary Examiner*—Amelia Owens
*Attorney, Agent, or Firm*—Stephen D. Harper

[57] ABSTRACT

Epoxides are produced by an integrated process involving molecular oxygen oxidation of a secondary alcohol, separation of the ketone co-product, and epoxidation of an olefin using the ketone-free oxidation product in the presence of a titanium silicalite catalyst and a methanol-containing diluent wherein methanol recovered from the epoxidation product mixture serves as a source of methanol in the epoxidation step.

18 Claims, 1 Drawing Sheet

INTEGRATED PROCESS FOR EPOXIDATION

FIELD OF THE INVENTION

This invention relates to an integrated process for producing an epoxide. In particular, the invention pertains to a titanium silicalite-catalyzed epoxidation method wherein methanol recovered from the epoxidation reaction mixture is used to dilute a concentrated oxidant stream used as a source of hydrogen peroxide in the epoxidation step.

BACKGROUND OF INVENTION

Many different methods for the preparation of epoxides have been developed. One such method involves the use of certain titanium silicalite materials to catalyze olefin oxidation by hydrogen peroxide. This method is described, for example, in U.S. Pat. No. 4,833,260, which discloses a procedure (Example 35) wherein propylene is converted to propylene oxide. An isopropanol/water mixture is reacted with oxygen at 135° C. to afford a mixture containing hydrogen peroxide. The mixture is thereafter used directly in a titanium silicalite-catalyzed epoxidation of propylene without intervening treatment or fractionation.

U.S. Pat. No. 5,384,418 describes an integrated process for epoxide production which also employs hydrogen peroxide derived from isopropanol oxidation in a titanium silicalite-catalyzed epoxidation, but teaches that removal of substantially all of the acetone from the isopropanol oxidant prior to use in epoxidation is advantageous. The patent additionally suggests that isopropanol derived from hydrogenation of the removed acetone could be employed to dilute the isopropanol oxidant to achieve the desired $H_2O_2$ feed concentration to the epoxidation reactor. Under certain conditions, it is desirable to maintain relatively dilute (i.e., 1-10 weight %) maximum hydrogen peroxide concentrations during epoxidation since higher concentrations can result in poorer epoxide selectivity. The patent does not, however, suggest the use of co-solvents (other than water, which may present as an azeotrope with the isopropanol) in such a process.

We have now discovered that the use of a recycled stream containing methanol to dilute, in effect, the hydrogen peroxide feed to the epoxidation zone is advantageous. Epoxide selectivity is improved due, it is believed, both to the diluting effort of said stream and also to the presence of methanol in said stream rather than other solvents which might in theory be used as diluents. That is, higher selectivity to epoxide is realized when the diluent is comprised of methanol rather than isopropanol, for example. Moreover, it has been found that the cost of operating such a co-solvent process is surprisingly low since the isopropanol and methanol may be readily separated from each other following epoxidation and individually recycled for use in different steps of a continuous process.

SUMMARY OF THE INVENTION

This invention provides an integrated epoxidation process comprising (a) reacting a $C_3$–$C_4$ secondary alcohol and molecular oxygen in a liquid phase to form an oxidant mixture comprised of the $C_3$–$C_4$ secondary alcohol, a $C_3$–$C_4$ ketone corresponding to the $C_3$–$C_4$ secondary alcohol, and hydrogen peroxide;

(b) separating substantially all of the $C_3$–$C_4$ ketone from the oxidant mixture to provide a concentrated hydrogen peroxide-containing stream comprised of $C_3$–$C_4$ secondary alcohol, hydrogen peroxide, and less than 1 weight percent $C_3$–$C_4$ ketone;

(c) reacting the concentrated hydrogen peroxide-containing stream with a $C_2$–$C_4$ olefin in the presence of a titanium silicalite catalyst and a diluent comprised of methanol to form an epoxidation reaction mixture comprised of a $C_2$–$C_4$ epoxide corresponding to the $C_2$–$C_4$ olefin, water, methanol, and $C_3$–$C_4$ secondary alcohol;

(d) separating substantially all of the $C_2$–$C_4$ epoxide from the epoxidation reaction mixture to form a first crude alcohol stream comprised of water, $C_3$–$C_4$ secondary alcohol, methanol and less than 1 weight percent of $C_2$–$C_4$ epoxide;

(e) separating substantially all of the methanol from the first crude alcohol stream to form a second crude alcohol stream comprised of water, $C_3$–$C_4$ secondary alcohol, and less than 1 weight percent methanol; and (f) recycling at least a portion of the methanol separated in step (e) for use as at least a portion of the diluent in step (c).

DETAILED DESCRIPTION OF THE INVENTION

Figure 1:
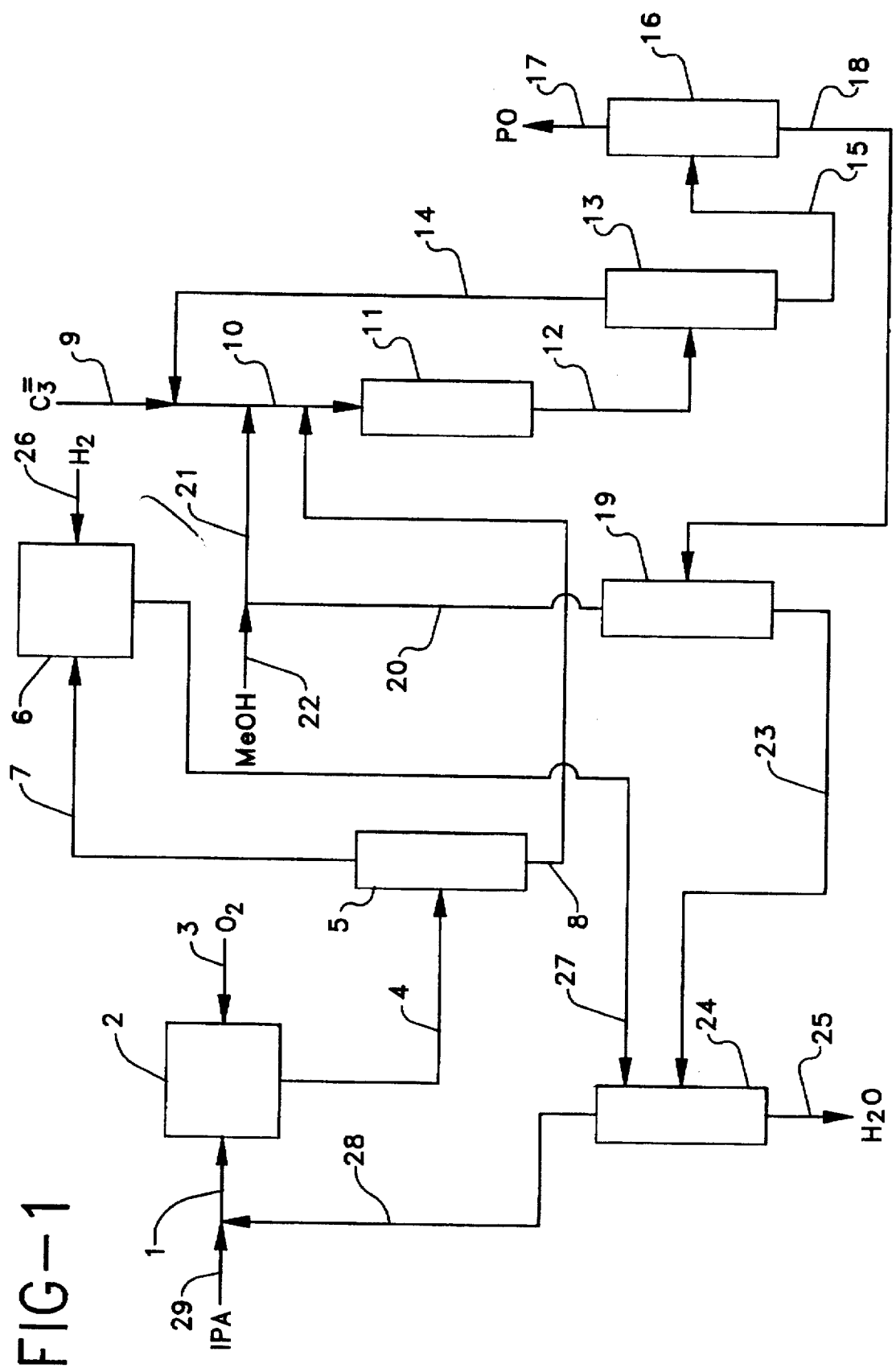
FIG. 1 illustrates in schematic form a suitable embodiment of the process of the invention.

The $C_3$–$C_4$ secondary alcohols suitable for use in the present invention include isopropanol (isopropyl alcohol) and sec-butanol (sec-butyl alcohol).

The secondary alcohol is reacted with molecular oxygen (dioxygen) from a suitable source such as air to yield an oxidant mixture, which will typically contain excess secondary alcohol, the $C_3$–$C_4$ ketone resulting from oxidation of the secondary alcohol and having the same hydrocarbon skeleton as the alcohol (e.g., acetone or 2-butanone), hydrogen peroxide and water. The starting material to be oxidized may contain minor amounts of the ketone and/or water in addition to the alcohol. For example, the azeotrope of water and isopropanol (87.8 wt % isopropanol, 12.2 wt % water) may be used to advantage. In one embodiment, the oxidizer feed comprises 5 to 20 weight % water, 80 to 95 weight % isopropanol, less than 1 weight % methanol, and less than 3 weight % acetone. Generally speaking, the oxidation conditions are adjusted so as to yield an oxidant mixture comprised of 40 to 90 weight percent secondary alcohol, from about 5 to 25 weight percent hydrogen peroxide, 5 to 35 weight percent of the ketone, and 0 to 35 weight percent water. Partial conversion of the secondary alcohol is accomplished (e.g., from 5 to 50%) such that the unreacted secondary alcohol may be utilized as a carrier or solvent for the hydrogen peroxide during subsequent steps of the process. Residence, hold-up or reaction times of from about 0.25 hours to 4 hours will typically be sufficient for this purpose. The oxidation may be either uncatalyzed or catalyzed (for example, by introduction of a minor amount of a peroxide or hydroperoxide such as t-butyl hydroperoxide). Temperatures of from 50° to 200° C. (more preferably, from 100 to 180° C.) will typically be appropriate for use in order to attain reasonable oxidation rates. The preferred range of oxygen partial pressure in the feed gases (which may include an inert diluent gas such as nitrogen in addition to oxygen) is 1 to 250 psia (more preferably, 5 to 50 psia; most preferably, 10 to 30 psia) partial pressure. Total pressure in the oxidation reaction zone should be sufficient to maintain the components of the reaction mixture in the liquid phase (50 psia to 1000 psia is normally sufficient). A plurality of oxidation reaction zones maintained at different temperatures may be employed. The alcohol oxidation may be performed in a continuous manner using, for example, a continuous stirred tank reactor (CSTR).

Prior to use in the epoxidation step of this process, the ketone is substantially separated or removed from the oxidant mixture. Any known separation method or technique which is suitable for this purpose may be utilized, including fractionation procedures.

Preferably, however, the oxidant mixture is fractionally distilled whereby the ketone is vaporized and removed from the oxidant mixture as an overhead stream. The concentrated hydrogen peroxide-containing stream obtained by such a procedure thus may comprise a bottoms fraction. Such fractionation may be facilitated by the application of heat and/or reduced (subatmospheric) pressure. The ketone concentration in the concentrated hydrogen peroxide-containing stream thereby produced should be less than 1 weight percent (more preferably, less than 0.5 weight percent). To minimize the formation of any ketone/hydrogen peroxide adducts having peroxy character, this separation is most preferably performed directly after molecular oxygen oxidation. Thus, the oxidant mixture exiting from the oxidizer zone is preferably taken into a distillation column without intervening storage or retention. To accomplish rapid and complete removal of the ketone from the oxidant mixture, it may be desirable to also take overhead some portion of the secondary alcohol and/or water. In one embodiment, for example, the overhead stream may comprise 10 to 80 mole % ketone, 15 to 60 mole % secondary alcohol, and 5 to 30 mole % water. However, for safety reasons, care must be taken not to overly concentrate the hydrogen peroxide in the bottoms fraction nor to have any appreciable amount of hydrogen peroxide in the overhead stream. The residence time in the distillation step is also important. The residence time must be sufficient to accomplish substantial reversal of any ketone/hydrogen peroxide reaction products generated during molecular oxygen oxidation or thereafter to bring the level of aliphatic ketone peroxides to less than 0.5 weight percent total. Excessive residence time should be avoided, however, to avoid decomposition of the hydrogen peroxide. In one preferred embodiment of the invention, a residence time of 10 to 45 minutes (more preferably, 15 to 30 minutes) at 90° to 130° C. (more preferably, 100° to 120° C.) is employed. Under these conditions, it has been found that the desired removal of ketone and conversion of any ketone peroxides present may be readily achieved with minimal loss (<2%) of the hydrogen peroxide in the oxidant mixture. Improved results may be obtained by carefully passivating the distillation column and/or treating the oxidant mixture so as to remove or counteract any species which might catalyze the decomposition of hydrogen peroxide or formation of ketone peroxides. Extractive distillation techniques may also be advantageously used. Other separation procedures capable of reducing the ketone content of the oxidant mixture without significant loss of the hydrogen peroxide contained therein may also be used including, for example, absorption, countercurrent extraction, membrane separation, and the like. Fractionation techniques wherein multiple stages are employed are especially suitable.

As a consequence of the removal of the ketone from the oxidant, the concentration of hydrogen peroxide is increased. The concentrated hydrogen peroxide-containing stream thus will typically contain from 5 to 30 weight percent $H_2O_2$. In one embodiment of the invention, said stream will be comprised of greater than 10 weight percent $H_2O_2$.

In the epoxidation step of the process of this invention, the concentrated hydrogen peroxide-containing stream is contacted with a $C_2$–$C_4$ olefin and a catalytically effective amount of a titanium silicalite at a temperature of from 25° C. to 120° C. (more preferably, 40° C. to 80° C.) to convert the substrate to the desired epoxide. A diluent comprised of methanol is also present, wherein methanol recovered from the epoxidation reaction mixture is utilized as at least a portion of said diluent. The remainder of the diluent, if any, may be fresh methanol, secondary alcohol obtained by hydrogenation of the ketone removed from the oxidant mixture, or fresh secondary alcohol or other such solvent. Preferably, the diluent is comprised predominantly (e.g., >70%) of methanol (primarily recycled methanol, with the amount of fresh methanol limited to the quantity needed to make up for the processing losses associated with methanol recovery). The amount of diluent employed preferably is sufficient to attain a methanol concentration of from 5 to 60 weight percent in the epoxidation reaction mixture (exclusive of the amount of olefin present).

Suitable $C_2$–$C_4$ olefins include ethylene, propylene, 1-butene, isobutylene, 2-butene and the like. Mixtures of olefins may be epoxidized if so desired.

The amount of olefin relative to the amount of hydrogen peroxide is not critical, but the molar ratio of olefin: hydrogen peroxide may suitably be from about 100:1 to 1:10. The molar ratio of olefin to hydrogen peroxide is more preferably in the range of from 1:2 to 10:1 (most preferably, 1:1 to 6:1). In one embodiment of the process of this invention, the feed to the epoxidation reactor (exclusive of the olefin to be epoxidized) comprises 1 to 10 weight percent hydrogen peroxide, 5 to 40 weight percent methanol, 30 to 85 weight percent secondary alcohol, and 1 to 25 weight percent water.

The titanium silicalites useful as catalysts in the epoxidation step of the process comprise the class of zeolitic substances wherein titanium is substituted for a portion of the silicon atoms in the lattice framework of a molecular sieve. Such substances are well-known in the art. Particularly preferred titanium silicalites include the classes of molecular sieves commonly referred to as "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta. The titanium silicalite preferably contains no non-oxygen atoms other than titanium and silica in the lattice framework, although minor amounts of boron, iron, aluminum, gallium, and the like may be present.

Epoxidation catalysts suitable for use in the process of this invention have a composition corresponding to the following empirical formula $xTiO_2:(1-x)SiO_2$, where x is between 0.0001 and 0.500. More preferably, the value of x is from 0.01 to 0.125. The molar ratio of Si:Ti in the lattice framework of the titanium silicalite is advantageously from 9.5:1 to 99:1 (most preferably, from 9.5:1 to 60:1). The use of relatively titanium-rich silicalites may be desirable.

The amount of catalyst employed is not critical, but should be sufficient so as to substantially accomplish the desired epoxidation reaction in a practicably short period of time. The optimum quantity of catalyst will depend upon a number of factors including reaction temperature, olefin reactivity and concentration, hydrogen peroxide concentration, type and concentration of organic solvent as well as catalyst activity and the type of reactor or reaction system (i.e., batch vs. continuous) employed. Typically, however, in a batch type epoxidation, the amount of catalyst will be from 0.001 to 10 grams per mole of olefin. In a fixed bed system, the optimum quantity of catalyst will be influenced by the flow rate of reactants through the fixed bed (generally, from about 1 to 100 moles $H_2O_2$ per kilogram of catalyst per hour).

The catalyst may be utilized in powder, pellet, microspheric, extruded, monolithic or any other suitable physical form. The use of a binder (co-gel) or support in combination with the titanium silicalite may be advantageous. Supported or bound catalysts may be prepared by the methods known in the art to be effective for zeolite catalysts in general. Preferably, the binder or support is essentially non-acidic and does not catalyze the non-selective decomposition of hydrogen peroxide or ring-opening of the epoxide.

The catalyst may be treated with an alkaline (basic) substance or a silylating agent so as to reduce the surface acidity, as described in U.S. Pat. No. 4,937,216.

The epoxidation reaction temperature is preferably from 25° C. to 120° C. (more preferably, from 40° C. to 80° C.), which in the process of this invention has been found to be sufficient to accomplish selective conversion of the olefin to epoxide within a reasonably short period of time with minimal non-selective decomposition of the hydrogen peroxide. It is generally advantageous to carry out the reaction to achieve as high a hydrogen peroxide conversion as possible, preferably at least 50%, more preferably at least 90%, most preferably at least 99%, consistent with reasonable selectivities. The optimum reaction temperature will be influenced by catalyst concentration and activity, substrate reactivity, reactant concentrations, and type of solvent employed, among other factors. Reaction or residence times of from about 10 minutes to 48 hours will typically be appropriate, depending upon the above-identified variables. The reaction is preferably performed at atmospheric pressure or at elevated pressure (typically, between 1 and 100 atmospheres). Generally, it will be desirable to maintain the reaction components as a liquid mixture. For example, when an olefin such as propylene is used having a boiling point at atmospheric pressure which is less than the epoxidation temperature, a superatmospheric pressure sufficient to maintain the desired concentration of propylene in the liquid phase should be utilized. At a reaction temperature of approximately 60° C., for instance, the pressure may advantageously be maintained at approximately 190–220 psig.

The epoxidation step of this invention may be carried out in a batch, continuous, or semi-continuous manner using any appropriate type of reaction vessel or apparatus such as a fixed bed, transport bed, stirred slurry, or CSTR reactor. Known methods for conducting metal-catalyzed epoxidations using hydrogen peroxide will generally also be suitable for use. Thus, the reactants may be combined all at once or sequentially. For example, the hydrogen peroxide, the diluent, and/or the olefin may be added incrementally to or at different points within the reaction zone. It will, however, generally be advantageous to control the addition of the various components such that the unreacted hydrogen peroxide concentration does not exceed 10 weight % at any point within the reaction zone.

After separating from the epoxidation reaction mixture by any suitable method such as filtration (as when a slurry reactor is utilized, for example), the recovered titanium silicalite catalyst may be economically re-used in subsequent epoxidations. Where the catalyst is deployed in the form of a fixed bed, the epoxidation product withdrawn as a stream from the epoxidation zone will be essentially catalyst free with the catalyst being retained within the epoxidation zone. In certain embodiments of the instant process where the epoxide is produced on a continuous basis, it may be desirable to periodically or constantly regenerate all or a portion of the used catalyst in order to maintain optimum activity and selectivity. Suitable regeneration techniques are well-known and include, for example, calcination and solvent treatment.

When the olefin and hydrogen peroxide have reacted to the desired level of conversion, the resulting epoxidation reaction mixture comprised of water, methanol, $C_2-C_4$ epoxide, and $C_3-C_4$ secondary alcohol is further treated so as to separate substantially all of the epoxide from the mixture to form a first crude alcohol stream comprised of water, methanol, $C_3-C_4$ secondary alcohol and less than 1 weight percent of the $C_2-C_4$ epoxide. The first crude alcohol stream is processed to form a second crude alcohol stream by removing substantially all of the methanol therefrom by a suitable separation method. Such separations may most readily be accomplished by distillative means (e.g., fractional distillation) as the secondary alcohol may be selected so as to be substantially higher boiling than the epoxide being produced and the methanol being utilized as diluent and thus amenable to recovery as a bottoms fraction. The methanol is vaporized and taken overhead. As the olefin is generally lower boiling than the epoxide, the secondary alcohol, and methanol, any unreacted olefin in the epoxidation reaction mixture may also be readily removed by distillation. In certain embodiments, the excess olefin may be removed together with epoxide by flash distillation. Fractional distillation or condensation is thereafter utilized to separate the olefin from the epoxide. In other embodiments, the olefin is first removed from the epoxidation reaction mixture, followed by the epoxide.

It is important to remove substantially (e.g., >95%; more preferably, >99%) of all the methanol from the first crude alcohol stream since methanol which is carried forward with the secondary alcohol will tend to be converted into formic acid during molecular oxygen oxidation of the secondary alcohol contained in the first crude alcohol stream. It is generally desirable to minimize acid formation during oxidation of the secondary alcohol because such acids may detrimentally affect epoxide selectivity when the oxidant mixture is used as a source of hydrogen peroxide in an epoxidation reaction.

Under certain conditions, it is possible for a minor amount of ketone by-product to be formed during epoxidation as a result of titanium silicalite-catalyzed oxidation of the secondary alcohol. Where the ketone by-product is acetone it may be removed from the first crude alcohol stream, if so desired, by fractional distillation or the like prior to recovery of the methanol. If the ketone by-product is 2-butanone, it may similarly be removed after methanol recovery from the second crude alcohol stream. The ketone by-product thus removed may be converted back to secondary alcohol for reuse by hydrogenation.

The methanol obtained from the first crude alcohol stream is thereafter recycled at least in part for use as at least a portion of the diluent in the epoxidation step. An important advantage of the process of this invention is that no further purification or processing of the recovered methanol is necessary prior to reuse in epoxidation in order to attain satisfactory results. Fractional distillation readily achieves substantially complete separation of the methanol from the other components of said stream.

The second crude alcohol stream may be recycled for use as a source of secondary alcohol in the oxidation step. Preferably, the second crude alcohol stream is first subjected to a further separation by means such as fractional distillation such that the portion of water corresponding to that generated as a co-product from hydrogen peroxide during epoxidation is removed in the form of a bottoms fraction with purified secondary alcohol (typically, as an azeotrope with water) being taken overhead.

In the hydrogenation step, the ketone separated from the oxidant mixture is converted back to the corresponding secondary alcohol by reacting the hydrogen in the presence of a transition metal hydrogenation catalyst. Methods of converting aliphatic ketones such as acetone and 2-butanone to their corresponding secondary aliphatic alcohols by catalytic hydrogenation using a transition metal catalyst and hydrogen gas are well-known.

The transition metal in the hydrogenation catalyst is most preferably palladium, platinum, chromium (as in copper chromite, for example), rhodium, nickel, or ruthenium. If water is present, the use of Raney nickel or molybdenum-promoted nickel is especially advantageous. The hydrogenation is suitably carried out in either a liquid or vapor phase.

The temperature, hydrogen pressure, and catalyst concentration during hydrogenation are selected so as to accomplish substantial (i.e., at least 80% and more preferably at least 95%) conversion of the ketone to secondary alcohol within a practicably short reaction time (i.e., approximately 15 minutes to 12 hours) without overreduction of the ketone. The optimum hydrogenation conditions will vary depending upon the type of catalyst selected for use and the reactivity of the ketone, but may be readily determined by one skilled in the art with minimal experimentation based on the known art pertaining to ketone hydrogenation. Typically, temperatures of from about 20° C. to 175° C. and hydrogen pressures of from about 0.5 to 100 atmospheres will be appropriate for use. Preferably, the molar ratio of $H_2$ to ketone is from about 1:1 to 4:1. The amount of catalyst employed is preferably sufficient to permit weight hourly space velocities of from 0.1 to 10 grams of ketone per gram of catalyst per hour.

The hydrogenation step may be carried out in a batch, semi-batch, continuous, or semi-continuous manner using any suitable reaction vessel or apparatus wherein the overhead stream may be intimately contacted with the transition metal hydrogenation catalyst and hydrogen. As the catalyst is normally heterogeneous in nature, fixed bed or slurry-type reactors are especially convenient for use. A trickle bed system may also be utilized.

FIG. 1 illustrates one embodiment of the integrated epoxidation process of the invention wherein propylene is catalytically epoxidized to yield propylene oxide. A stream comprised of secondary alcohol passes via line 1 into alcohol oxidation zone 2 wherein the secondary alcohol is partially reacted with molecular oxygen to form an oxidant mixture comprised of hydrogen peroxide, ketone, and excess secondary alcohol. The molecular oxygen is provided by air or pure or diluted $O_2$ introduced via line 3.

The oxidant mixture containing hydrogen peroxide, ketone, and secondary alcohol passes from zone 2 via line 4 into oxidant distillation zone 5. In 5, the oxidant mixture is subjected to fractional distillation. Ketone is taken overhead (together, in some cases, with a portion of the secondary alcohol) and into hydrogenation zone 6 via line 7. The bottoms fraction (i.e., the concentrated hydrogen peroxide-containing stream), which contains hydrogen peroxide and secondary alcohol, is carried forward via line 8 for use in epoxidation.

The olefin to be epoxidized is fed into epoxidation zone 11 by way of lines 9 and 10. In the particular embodiment shown on FIG. 1, lines 8 and 21 also feed into line 10 at points separated from line 9. However, numerous other ways of introducing the various feed streams into epoxidation zone 11 are feasible. For example, the contents of lines 8 and 21 may be combined in a common line prior to entering line 10. Alternatively, the olefin, the recycled methanol (diluent), and the concentrated hydrogen peroxide-containing stream may be separately introduced directly into epoxidation zone 11. The precise manner in which the various reaction components are introduced into the epoxidation zone thus is not critical, provided that the net effect is to dilute the concentrated hydrogen peroxide-containing stream with methanol.

The titanium silicalite catalyst is preferably deployed in zone 11 as a fixed bed, although a slurry configuration could also be employed. The olefin, concentrated hydrogen peroxide-containing stream and diluent are maintained at the desired reaction temperature in contact with the titanium silicalite within zone 11 for a time sufficient to convert at least a portion of the olefin to the corresponding $C_3$–$C_4$ epoxide, thereby consuming most or all of the hydrogen peroxide and generating water as a co-product. The epoxidation reaction mixture thus produced passes through line 12 to olefin recovery zone 13 wherein unreacted olefin is separated by an appropriate means such as distillation and recycled to epoxidation zone 11 via lines 14 and 10. The remainder of the epoxidation reaction mixture is taken on via line 15 to epoxide purification zone 16 wherein the propylene oxide is separated by an appropriate means such as distillation and removed via line 17. Removal of the epoxide and unreacted olefin from the epoxidation reaction mixture generates a first crude alcohol stream comprised of isopropanol, methanol, and heavier substances such as water, acids, glycols, and the like but little if any propylene oxide. The first crude alcohol stream is transported from epoxide purification zone 16 via line 18 and introduced into crude alcohol purification zone 19. Within zone 19, the methanol is separated from the first crude alcohol stream by an appropriate means such as distillation. The separated methanol (which may, for example, be taken overhead as a light fraction during distillation) is recycled for use as diluent in epoxidation zone 11 via lines 20 and 21. Make-up methanol, if needed, may be combined with the recycled methanol through line 22.

The second crude alcohol stream which is generated by removal of the methanol from the first crude alcohol stream in zone 19 is carried via line 23 into secondary alcohol purification zone 24. Secondary alcohol purification zone 24 is operated such that the purified secondary alcohol (or, in some embodiments, an azeotrope of the secondary alcohol with water) is taken overhead and an aqueous stream containing at least a portion of the water generated as a co-product from the hydrogen peroxide during epoxidation as well as the heavier epoxidation by-products (acids, glycols) is generated as a bottoms fraction and withdrawn via line 25. The purified secondary alcohol is recycled back to alcohol oxidation zone 2 via lines 28 and 1. Make-up secondary alcohol may be introduced using line 29.

The overhead stream from oxidant distillation zone 5 is passed via line 7 into hydrogenation zone 6 wherein the stream is reacted with hydrogen (introduced via line 26) in the presence of a suitable hydrogenation catalyst such as supported ruthenium or molybdenum—promoted Raney nickel (preferably deployed as a fixed bed within zone 6) so as to convert at least a portion and preferably substantially all (e.g., over 95%) of the ketone back to secondary alcohol. The hydrogenation stream withdrawn from zone 6 via line 27 may be, if so desired, further purified (for example, in alcohol purification zone 24) or alternatively, may be passed directly back to alcohol oxidation zone 2.

From the foregoing description, one skilled in the art can readily ascertain the essential characteristics of this invention, and, without departing from the spirit and scope thereof, can make various changes and modifications of the invention to adapt it to various usages, conditions, and embodiments.

We claim:

1. An integrated epoxidation process comprising
   (a) reacting a $C_3$–$C_4$ secondary alcohol and molecular oxygen in a liquid phase to form an oxidant mixture comprised of $C_3$–$C_4$ secondary alcohol, a $C_3$–$C_4$ ketone corresponding to the $C_3$–$C_4$ secondary alcohol, and hydrogen peroxide;
   (b) separating substantially all of the $C_3$–$C_4$ ketone from the oxidant mixture to provide a concentrated hydrogen peroxide-containing stream comprised of $C_3$–$C_4$ secondary alcohol, hydrogen peroxide, and less than 1 weight percent $C_3$–$C_4$ ketone;
   (c) reacting the concentrated hydrogen peroxide-containing stream with a $C_2$–$C_4$ olefin in the presence of a titanium silicalite catalyst and a diluent comprised of methanol to form an epoxidation reaction mixture comprised of a $C_2$–$C_4$ epoxide corresponding to the $C_2$–$C_4$ olefin, water, methanol, and $C_3$–$C_4$ secondary alcohol;
   (d) separating substantially all of the $C_2$–$C_4$ epoxide from the epoxidation reaction mixture to form a first crude alcohol stream comprised of water, $C_3$–$C_4$ secondary alcohol, methanol, and less than 1 weight percent of $C_2$–$C_4$ epoxide;
   (e) separating substantially all of the methanol from the first crude alcohol stream to form a second crude alcohol stream comprised of water, $C_3$–$C_4$ secondary alcohol, and less than 1 weight percent methanol; and
   (f) recycling at least a portion of the methanol separated in step (e) for use as at least a portion of the diluent in step (c).

2. The integrated epoxidation process of claim 1 wherein the $C_3$–$C_4$ ketone separated from the oxidant mixture in step (b) is hydrogenated to the $C_3$–$C_4$ secondary alcohol.

3. The integrated epoxidation process of claim 1 wherein the $C_2$–$C_4$ olefin is propylene.

4. The integrated epoxidation process of claim 1 wherein the $C_3$–$C_4$ secondary alcohol is isopropanol.

5. The integrated epoxidation process of claim 1 wherein the concentrated hydrogen peroxide-containing stream is comprised of greater than 5 and less than 30 weight percent hydrogen peroxide.

6. The integrated epoxidation process of claim 1 wherein the amount of diluent is sufficient to provide a hydrogen peroxide concentration of from 1 to 10 weight percent in step (c) based on the total weight of the concentrated hydrogen peroxide-containing stream and diluent.

7. The integrated process of claim 1 wherein the titanium silicalite has an MFI, MEL, or zeolite beta topology.

8. The integrated epoxidation process of claim 1 wherein the titanium silicalite has a composition corresponding to the chemical formula $xTiO_2:(1-x) SiO_2$ wherein x is from 0.01 to 0.125.

9. The integrated epoxidation process of claim 1 wherein separation step
   (b) is accomplished by distillation whereby substantially all of the $C_3$–$C_4$ ketone is vaporized and removed from the oxidant mixture as an overhead stream.

10. The integrated epoxidation process of claim 1 wherein step (a) is performed at a temperature of from 50° C. to 200° C.

11. The integrated epoxidation process of claim 1 wherein step (c) is performed at a temperature of from 25° C. to 120° C.

12. The integrated epoxidation process of claim 1 comprising the additional step of recycling at least a portion of the $C_3$–$C_4$ secondary alcohol in the second crude alcohol stream for use in step (a).

13. The integrated epoxidation process of claim 12 wherein at least a portion of the water in the second crude alcohol stream is separated from the $C_3$–$C_4$ secondary alcohol prior to recycling for use in step (a).

14. An integrated epoxidation process comprising
   (a) reacting isopropanol and molecular oxygen in a liquid phase at a temperature of from 50° C. to 200° C. to form an oxidant mixture comprised of isopropanol, acetone, and hydrogen peroxide;
   (b) subjecting the oxidant mixture to distillation whereby substantially all of the acetone is vaporized and removed from the oxidant mixture as an overhead stream so as to provide a concentrated hydrogen peroxide-containing stream comprised of isopropanol, greater than 5 and less than 30 weight percent hydrogen peroxide, and less than 1 weight percent acetone;
   (c) reacting the concentrated hydrogen peroxide-containing stream with propylene at a temperature of from 40° C. to 80° C. in the presence of a titanium silicalite catalyst and a diluent comprised of methanol to form an epoxidation reaction mixture comprised of water, propylene oxide, methanol, and isopropanol;
   (d) separating substantially all of the propylene oxide from the epoxidation reaction mixture by distillation to form a first bottoms stream comprised of water, methanol, isopropanol and less than 1 weight percent of propylene oxide;
   (e) separating substantially all of the methanol from the first bottoms stream by distillation to form a second bottoms stream comprised of water, isopropanol, and less than 1 weight percent methanol;
   (f) recycling at least a portion of the methanol separated in step (e) for use as at least a portion of the diluent in step (c);
   (g) separating at least a portion of the water from the second bottoms stream to form a crude isopropanol stream;
   (h) hydrogenating the acetone separated from the oxidant mixture in step (b) to isopropanol; and
   (i) recycling the crude isopropanol stream and the isopropanol obtained in step (h) for use in step (a).

15. The integrated epoxidation process of claim 14 wherein step (h) is performed in the presence of a hydrogenation catalyst comprised of a transition metal selected from palladium, platinum, ruthenium, chromium, rhodium, and nickel at a temperature of 20° to 175° C. and a hydrogen pressure of 0.5 to 100 atmospheres.

16. The integrated epoxidation process of claim 14 wherein the titanium silicalite is deployed in the form of a fixed bed.

17. The integrated epoxidation process of claim 14 wherein the molar ratio of propylene: hydrogen peroxide in step (c) is from 1:2 to 10:1.

18. The integrated epoxidation process of claim 14 wherein methanol comprises from 5 to 60 weight percent of the epoxidation reaction mixture.

* * * * *